United States Patent
Zhang et al.

(10) Patent No.: US 11,091,381 B1
(45) Date of Patent: Aug. 17, 2021

(54) METHOD FOR EXTRACTING ANTIBACTERIAL PEPTIDES AND ALBUMIN FROM PEA WHEY WASTEWATER

(71) Applicant: YANTAI SHUANGTA FOOD CO., LTD., Shandong (CN)

(72) Inventors: Shucheng Zhang, Shandong (CN); Jinjie Yang, Shandong (CN); Qingjia Zang, Shandong (CN); Shimin Wu, Shandong (CN); Guodong Yang, Shandong (CN)

(73) Assignee: YANTAI SHUANGTA FOOD CO., LTD., Yantai (CN)

( * ) Notice: Subject to any disclaimer, the term of this patent is extended or adjusted under 35 U.S.C. 154(b) by 0 days.

(21) Appl. No.: 17/169,542

(22) Filed: Feb. 7, 2021

(30) Foreign Application Priority Data

Mar. 9, 2020 (CN) .......................... 202010154908.3

(51) Int. Cl.

| | |
|---|---|
| *A23J 1/16* | (2006.01) |
| *B01D 1/26* | (2006.01) |
| *B01D 61/02* | (2006.01) |
| *B01D 61/14* | (2006.01) |
| *B01D 61/58* | (2006.01) |
| *B01D 69/02* | (2006.01) |
| *C02F 1/00* | (2006.01) |
| *C02F 1/38* | (2006.01) |
| *C02F 1/44* | (2006.01) |
| *C02F 1/66* | (2006.01) |
| *C02F 103/32* | (2006.01) |
| *C02F 9/00* | (2006.01) |
| *C07K 1/36* | (2006.01) |
| *C07K 14/415* | (2006.01) |
| *B01D 71/02* | (2006.01) |
| *C02F 1/06* | (2006.01) |
| *C02F 101/38* | (2006.01) |

(52) U.S. Cl.
CPC ........ *C02F 9/00* (2013.01); *A23J 1/16* (2013.01); *B01D 1/26* (2013.01); *B01D 61/022* (2013.01); *B01D 61/027* (2013.01); *B01D 61/142* (2013.01); *B01D 61/145* (2013.01); *B01D 61/147* (2013.01); *B01D 61/58* (2013.01); *B01D 69/02* (2013.01); *B01D 71/021* (2013.01); *C07K 1/36* (2013.01); *C07K 14/415* (2013.01); *B01D 2311/2649* (2013.01); *B01D 2311/2673* (2013.01); *B01D 2311/2676* (2013.01); *B01D 2311/2692* (2013.01); *B01D 2325/02* (2013.01); *B01D 2325/20* (2013.01); *C02F 1/001* (2013.01); *C02F 1/06* (2013.01); *C02F 1/38* (2013.01); *C02F 1/442* (2013.01); *C02F 1/444* (2013.01); *C02F 1/66* (2013.01); *C02F 2101/38* (2013.01); *C02F 2103/32* (2013.01); *C02F 2301/08* (2013.01)

(58) Field of Classification Search
CPC .......... A23J 1/16; B01D 61/022; C02F 1/442; C02F 1/444; C02F 2103/32
See application file for complete search history.

(56) References Cited

U.S. PATENT DOCUMENTS

2015/0368293 A1* 12/2015 Barata .................... B01D 61/16
530/370

FOREIGN PATENT DOCUMENTS

CN        103113459 A      5/2013

OTHER PUBLICATIONS

Qin Xiangdong—CN103113459A Machine Translation—May 22, 2013 (Year: 2013).*
Gao, Lei Leigh, Khai D. Nguyen, and Alphonsus C. Utioh. "Pilot scale recovery of proteins from a pea whey discharge by ultrafiltration." LWT-Food Science and Technology 34.3 (2001): 149-158. (Year: 2001).*
First Office Action of Counterpart Chinese Patent Application No. 202010154908.3 dated Apr. 26, 2020.
Notification to Grant Patent Right of counterpart Chinese Patent Application No. 202010154908.3 dated May 21, 2020.
Wang Duoren, Organic Food Nutrition Enhancer, Beijing: Scientific and Technical Documentation Press, Aug. 31, 2008, p. 378.
Soy peptide powder, National Standards of PRC, General Administration of Quality Supervision, Inspection and Quarantine of the Peoples Republic of China, Standardization Administration, Nov. 4, 2008, pp. 1-9, GB/T 22492-2008.

* cited by examiner

*Primary Examiner* — Bradley R Spies

(57) ABSTRACT

The disclosure provides a method for extracting antibacterial peptides and albumin from pea whey wastewater, which includes following steps: in extracting the albumin, centrifuging with the pea whey wastewater generated during pea protein processing as raw material; controlling temperature and exchanging heat to adjust temperature of the raw material; sequentially performing a microfiltrating, nanofiltration, ultrafiltration and secondary nanofiltration to obtain an albumin slurry; performing a multi-effect concentration on the albumin slurry; adding an alkaline substances to adjust pH; sterilizing and drying to finally obtain the albumin, which realizes a targeted extraction of the albumin with small molecular weight in the pea whey wastewater and avoids resource waste. The albumin with small molecular weight and the antibacterial peptides in the pea whey water are effectively recycled, thus avoiding environmental pollution caused by improper treatment of the pea whey water and realizing resource reuse.

15 Claims, No Drawings ered; separating the antibacterial peptides; controlling

METHOD FOR EXTRACTING ANTIBACTERIAL PEPTIDES AND ALBUMIN FROM PEA WHEY WASTEWATER

CROSS REFERENCE TO RELATED APPLICATIONS

The present application claims the benefit of Chinese Patent Application No. 202010154908.3 filed on Mar. 9, 2020, the contents of which are incorporated herein by reference in their entirety.

TECHNICAL FIELD

The disclosure belongs to the technical field of protein extraction, and particularly relates to a method for extracting antibacterial peptides and albumin from pea whey wastewater.

BACKGROUND ART

Pea, as a crop with high starch content, is commonly used as a raw material for vermicelli and glass noodles. Pea whey wastewater is the one from a production of pea isolated proteins. To get every ton of the isolated protein, 25 to 35 cubic meters of the pea whey wastewater may be discharged, and domestic pea isolated protein production enterprises produce more than 13 million tons of the pea whey every year, which is of great amount.

The pea whey wastewater contains large amount of ammonia nitrogen and COD, with ammonia nitrogen up to 700 and both COD (chemical oxygen demand) and BOB (biological oxygen demand) higher than 10,000. Typically, a large number of flocculants, such as polyacrylamide and polyaluminium chloride, are necessary to be added in treating the pea whey wastewater which is then subjected to a flocculation flotation process followed by a water removal with a plate and frame filter press, and handled as solid waste or sold as feed or raw material of fermentation industries after treatment. However, the above-described treatment process presents low technical added value, and economic benefits brought by products of the process are low, resulting in resource waste; at the same time, due to an addition of a large number of flocculants, there are safety risks and potential safety hazards.

Currently, there is a method to treat the pea whey wastewater in which the isolated protein is recycled and an isoelectric-point acid precipitation is employed. However, after recovering pea isolated protein, the residual pea whey wastewater still contains protein components with small molecular weight, which cannot be effectively extracted and utilized.

The protein with small molecular weight in the whey can function to improve immunity and oxidation resistance, etc, which can be extracted and applied as raw material of health food and has high nutrition and utilization value. If the protein cannot be extracted effectively, not only the protein in the pea whey is wasted, but also an albumin loss, and thus environmental pollution, is caused.

However, it is still difficult to effectively recycle the albumin with small molecular weight due to physical properties of pea whey proteins. There are few researches on the recycling and treatment methods of the pea whey proteins. In the prior art, pea proteins or polypeptides are prepared and extracted by enzymatic hydrolysis technologies. For these technologies, firstly, target products are different; secondly, if the enzymatic hydrolysis technologies are applied to extract the albumin from the pea whey, a bitter taste occurs in the protein and mouthfeel is affected; furthermore, the extracted protein or polypeptides are not conducive to human absorption and utilization. In addition, in other methods of separating and purifying whey proteins, the whey proteins are often extracted from wastewater in soybean production, and because these methods are applied to different initial raw material from the pea whey, these methods cannot be directly converted and used in the pea whey, and thus recycling rate and purity of the pea albumin cannot be guaranteed for these methods.

Antibacterial peptide is a kind of polypeptide with antibacterial activity, which acts on bacterial cell membrane, destroys its integrity, produces perforation, enters the cell and destroys its organelles, and causes metabolic disorder. The antibacterial peptide not only has good bactericidal effect on bacteria and fungi, but also has antiviral activity and promotes wound healing. Although the antibacterial peptide has broad application prospects and great development potentials, an industrialization of the antibacterial peptide advances slowly. Currently, a main method to produce the antibacterial peptide involves genetic engineering technologies, for which production cost is high, the produced antibacterial peptide is easy to be hydrolyzed and its industrialization scale needs to be broken through. Moreover, the produced antibacterial peptide has low activity, poor heat resistance and thermal stability.

Currently, in treating the pea whey water, there are no other treating methods except separating various proteins, which also causes loss of the antibacterial peptide.

SUMMARY

The disclosure provides a method for extracting antibacterial peptides and albumin from pea whey wastewater, which solves problems described in the background art of resource waste, low recycling and utilization rate of the albumin, no target extraction of the albumin, and loss of the antibacterial peptides due to an inability to extract the albumin with small molecular weight from the pea whey wastewater.

A specific technical scheme is as follows.

A method for extracting the antibacterial peptides from pea whey wastewater is provided, which includes following steps:

centrifuging with the pea whey wastewater generated during pea protein processing as raw material; controlling temperature and exchanging heat to adjust temperature of the raw material;

sequentially performing a microfiltrating, nanofiltration, ultrafiltration and secondary nanofiltration to obtain an albumin slurry; performing a multi-effect concentration on the albumin slurry; adding an alkaline substance to adjust pH; sterilizing and drying to obtain the albumin;

adding water to the albumin to obtain another albumin slurry, pretreating in water bath, cooling and stirring on a constant temperature magnetic stirrer, adding papain and dipping alkali solution to keep pH of enzymatic hydrolysate constant; boiling to inactivate enzyme after full enzymolysis and cooling, adjusting the pH to 7.0; centrifuging and concentrating supernatant by rotary evaporation, and sterilizing with a 0.22 μm syringe filter to obtain primary product of the antibacterial peptides; and passing the primary product of the antibacterial peptides through an extractor, which is cleaned and activated in advance with methanol aqueous solution and then cleaned and balanced by aqueous trifluoroacetic acid solution;

sequentially passing the methanol aqueous solution and the aqueous trifluoroacetic acid solution through the extractor and collecting penetrating liquid, vacuum concentrating the penetrating liquid by a rotary evaporator to get concentrated antibacterial peptide solution, taking out the concentrated antibacterial peptide solution and freezing at −15° C., and drying the frozen antibacterial peptides in a vacuum freeze dryer to obtain purified antibacterial peptides.

The antibacterial peptides have following features that: PH value of the antibacterial peptides is 2.56 to 2.78, as measured by a pH meter.

An antibacterial peptide molecule contains glycine, cysteine, arginine, lysine, histidine, alanine, threonine, aspartic acid, leucine, phenylalanine, serine, glutamic acid, valine, methionine, or tyrosine.

A method for extracting antibacterial peptides from pea whey wastewater includes following steps: centrifuging with the pea whey wastewater generated during pea protein processing as raw material; controlling temperature and exchanging heat to adjust temperature of the raw material; sequentially performing a microfiltrating, nanofiltration, ultrafiltration and secondary nanofiltration to obtain an albumin slurry; performing a multi-effect concentration on the albumin slurry; adding an alkaline substances to adjust pH; and sterilizing and drying to obtain the albumin.

Preferably, the method specifically includes following steps:

1) the centrifuging: centrifuging with the pea whey wastewater as the raw material;

2) the controlling temperature and exchanging heat: performing a heat exchange on the centrifuged pea whey wastewater;

3) the performing the microfiltration: performing the microfiltration on the pea whey wastewater after the heat exchange;

4) the performing the nanofiltration: removing 93% to 95% of water in the pea whey wastewater after the microfiltration by using a nanofiltration module and adjusting system pressure and filtration temperature;

5) the performing the ultrafiltration: eluting and separating for 5 to 10 times with an ultrafiltration membrane to obtain a crude albumin slurry;

6) the performing the secondary nanofiltration: washing the crude albumin with clean water added and using an anti-pollution nanofiltration membrane, and removing the clean water for washing after the washing is complete;

7) the performing the multi-effect concentration: adding the washed albumin slurry into an evaporator for evaporation and concentration;

8) the adjusting the pH: adding the alkaline substance and adjusting the pH 9) sterilizing and drying.

Preferably, the temperature in controlling temperature and exchanging heat is 40 to 50° C.

Preferably, a membrane used in the microfiltration is a silicon carbide membrane or a ceramic membrane.

Preferably, a pore size of the silicon carbide film is 10 nanometers to 30 micrometers.

Preferably, during the nanofiltration, the system pressure is adjusted to 18 to 25 bar, and the filtration temperature is 40 to 65° C.

Preferably, during the ultrafiltration, a pore size of the ultrafiltration membrane is configured to provide a molecular weight cut-off of 1000 to 5000 Daltons.

Preferably, during the secondary nanofiltration, the clean water for washing is the water of 93% to 95% obtained in the nanofiltration in step 4).

Preferably, during the multi-effect concentration, a vapor pressure is 0.6-0.8 MPa, and a concentration of the concentrated albumin slurry is 25% to 50%; during the adjusting the pH, the alkaline substance is added at a temperature of 40 to 65° C. to adjust the pH to be 6.5 to 8.

Beneficial Effects

1. According to the disclosure, by setting the whole process flow, a targeted extraction of the albumin with small molecular weight is carried out in the pea whey water. The pea whey water is centrifuged followed by temperature controlling and heat exchanging so that macromolecular proteins in the pea whey water can be separated, which ensures that the albumin and pea oligosaccharides enter a next process without blocking devices, thus laying a foundation for providing a relatively averaged albumin molecular weight subsequently.

2. In the ultrafiltration, a pore size of the ultrafiltration membrane is configured to provide a molecular weight cut-off of 1000 to 5000 Daltons so as to ensure that the molecular weight of the separated albumin is concentrated in a range of 1000 to 5000 Daltons, in which the albumin with a molecular weight within the range of 1000-5000 Daltons accounts for 85%, and the molecular weight is relatively average and small, and the albumin is easy to be absorbed and utilized by human body.

3. The temperature controlling and heat exchanging were carried out before the microfiltration to keep the temperature of the whey water stable and make it reach an optimum operating temperature before the microfiltration, thus laying a foundation for subsequent effective separation. In the microfiltration, macromolecular proteins that were not separated by centrifuging in the pea whey water were further separated, laying a foundation for the subsequent nanofiltration. In the nanofiltration, the nanofiltration module is used to further separate the albumin and remove 93% to 95% of water at the same time, and after the nanofiltration, the albumin still contains a small amount of oligosaccharides; at this time, the ultrafiltration is carried out to separate the albumin from the oligosaccharides. However, at this time, the albumin still contains excess salt, which leads to a lower albumin purity. Then, the secondary nanofiltration is carried out, in which the sanitary anti-pollution nanofiltration membrane is adopted, and the clean water separated during the nanofiltration is added for washing to elute the excess salt, and after washing is complete, the clean water is separated and recycled. With a series of steps described above, the albumin with small molecular weight in the pea whey water can be effectively recycled with a higher purity, thus avoiding environmental pollution caused by improper treatment of the pea whey water and realizing resource reuse.

4. In the present disclosure, the conventional enzymolysis process is not adopted, and the albumin is guaranteed with a good mouthfeel to a maximum extent, with a high product recycling rate and without bitterness or off-flavors, thus presenting high product quality. According to the disclosure, a physical extraction mode is adopted with no chemical reaction involved, so that amino acids in the albumin are maintained relatively complete, and the albumin contains various amino acids, has similar amino acid content with pure albumin, and thus presents good product performance and high nutritional value.

5. In this scheme, the macromolecular proteins in bean whey water is removed with various separation and water washing processes, which effectively reduces interference of the macromolecular proteins on subsequent albumin separation process and ensures the purity of the albumin. In this process, a desalination process is adopted, in which the salt in the albumin is washed with the water and separated by the nanofiltration membrane to remove sour taste of the whey proteins.

6. In the present disclosure, the nanofiltration module is used to further separate the albumin and remove 93% to 95% of water at the same time, and this water can be recycled and used in the secondary nanofiltration, which removes a sewage treatment process and saves energy and water resources.

7. In this disclosure, the pea whey water in the pea protein processing process is used, and two ways for recycling the pea whey water are provided, which can not only extract antibacterial peptides, but also extract the albumin with small molecular weight, thus improving recycling and utilization rate of the pea whey water. In addition, the method for extracting the antibacterial peptides provided in the disclosure can not only take the bean whey water as raw material, but also take the albumin extracted in the disclosure as raw material for reprocessing, so as to extract the antibacterial peptides with good heat resistance and thermal stability.

8. When the antibacterial peptide is extracted, the papain is added, and NaOH is dripped at any time to keep the pH of the enzymatic hydrolysate constant; a complete enzymolysis reaction is made for 5 to 8 h followed by boiling for 15 min and cooling, and adjusting the pH to 7.0 with NaOH or HCl; then the centrifuging is carried out at 8500 r/min for 20 min to remove the precipitate, followed by spin evaporating and concentrating the supernatant, and sterilizing with the 0.22 μm syringe filter, which can effectively control degree of protein hydrolysis and will not destroy the amino acids in the polypeptides, making the antimicrobial peptides rich in various amino acids, not easy to denature after being heated, and having good heat resistance and thermal stability.

DETAILED DESCRIPTION

In the following, the present disclosure will be described in detail and clearly in combination with various embodiments 1. Extraction of Antibacterial Peptides According to the disclosure, the bean whey water in the pea protein processing process is adopted, and two ways for recycling the bean whey water are provided, in which the bean whey water is centrifuged and then heat exchanged followed by a microfiltration to obtain retentate, the retentate is then used for extracting antibacterial peptides and a slurry after the microfiltration is used for extracting albumin. In this way, not only the antibacterial peptides but also the albumin with small molecular weight can be extracted, thus improving recycling and utilization rate of the pea whey water. In addition, the method for extracting the antibacterial peptides provided in the disclosure can not only take the bean whey water as raw material, but also take the albumin extracted in the disclosure as raw material for reprocessing, so as to extract the antibacterial peptides with good heat resistance and thermal stability. In the following, the present disclosure will be described in detail and clearly in combination with various embodiments A method for extracting the antibacterial peptides from the pea whey wastewater includes following steps: centrifuging with the pea whey wastewater generated during pea protein processing as raw material; performing a heat exchange on the centrifuged pea whey water; and performing a microfiltration on the pea whey water after the heat exchange, in which a silicon carbide membrane with a pore size of 10 nanometers to 30 microns is adopted in the microfiltration process and a retentate is reserved;

pretreating the retentate in 85° C. water bath for 15 min, cooling and stirring on a constant temperature magnetic stirrer, adding papain and dripping NaOH at any time to keep pH of the enzymatic hydrolysate constant; boiling for 15 min after full enzymolysis for 5 to 8 h and cooling, and adjusting the pH to 7.0 with NaOH or HCl; centrifuging at 8500 r/min for 20 min to remove precipitates, concentrating supernatant by rotary evaporation, and sterilizing with a 0.22 μm syringe filter to obtain primary product of the antibacterial peptides;

passing the primary product of the antibacterial peptides through an extractor, which is cleaned and activated in advance with methanol aqueous solution and then cleaned and balanced by aqueous trifluoroacetic acid solution; sequentially passing the methanol aqueous solution and the aqueous trifluoroacetic acid solution through the extractor and collecting penetrating liquid, vacuum concentrating the penetrating liquid by a rotary evaporator to get concentrated antibacterial peptide solution, taking out the concentrated antibacterial peptide solution and freezing at −15° C. for 9 to 12 h, and drying the frozen antibacterial peptides for 20 to 25 hours in a vacuum freeze dryer, with vacuum degree controlled to be 30 to 50 Pa, to obtain purified antibacterial peptides.

Example 1

The method includes following steps of: centrifuging with the pea whey wastewater generated during pea protein processing as the raw material; performing a heat exchange on the centrifuged pea whey water; and performing a microfiltration on the pea whey water after the heat exchange, in which a silicon carbide membrane with a pore size of 20 microns is adopted in the microfiltration process and a retentate is reserved;

pretreating the retentate in 85° C. water bath for 15 min, cooling and stirring on a constant temperature magnetic stirrer, adding papain and dripping NaOH at any time to keep pH of the enzymatic hydrolysate constant; boiling for 15 min after full enzymolysis for 7 h and cooling, and adjusting the pH to 7.0 with NaOH or HCl; centrifuging at 8500 r/min for 20 min to remove the precipitates, concentrating supernatant by rotary evaporation, and sterilizing with a 0.22 μm syringe filter to obtain primary product of the antibacterial peptides;

passing the primary product of the antibacterial peptides through an extractor, which is cleaned and activated in advance with methanol aqueous solution and then cleaned and balanced by aqueous trifluoroacetic acid solution; sequentially passing the methanol aqueous solution and the aqueous trifluoroacetic acid solution through the extractor and collecting penetrating liquid, vacuum concentrating the penetrating liquid by a rotary evaporator to get concentrated antibacterial peptide solution, taking out the concentrated antibacterial peptide solution and freezing at −15° C. for 10 h, and drying the frozen antibacterial peptides for 20 h in a vacuum freeze dryer, with vacuum degree controlled to be 40 Pa, to obtain purified antibacterial peptides.

Example 2

The method includes following steps: centrifuging with the pea whey wastewater generated during pea protein processing as raw material; controlling temperature and exchanging heat to adjust temperature of the raw material;

sequentially performing a microfiltrating, nanofiltration, ultrafiltration and secondary nanofiltration to obtain an albumin slurry; performing a multi-effect concentrating on the albumin slurry; adding an alkaline substances to adjust pH; sterilizing and drying to obtain the albumin;

adding water to the albumin to obtain an albumin slurry, pretreating in 85° C. water bath for 15 min, cooling and stirring on a constant temperature magnetic stirrer, adding papain and dripping NaOH at any time to keep pH of the enzymatic hydrolysate constant; boiling for 15 min after full enzymolysis for 5 to 8 h and cooling, and adjusting the pH to 7.0 with NaOH or Hcl; centrifuging at 8500 r/min for 20 min to remove precipitates, concentrating supernatant by rotary evaporation, and sterilizing with a 0.22 μm syringe filter to obtain primary product of the antibacterial peptides;

passing the primary product of the antibacterial peptides through an extractor, which is cleaned and activated in advance with methanol aqueous solution and then cleaned and balanced by aqueous trifluoroacetic acid solution; sequentially passing the methanol aqueous solution and the aqueous trifluoroacetic acid solution through the extractor and collecting penetrating liquid, vacuum concentrating the penetrating liquid by a rotary evaporator to get concentrated antibacterial peptide solution, taking out the concentrated antibacterial peptide solution and freezing at −15° C. for 9 to 12 h, and drying the frozen antibacterial peptides for 20 to 25 hours in a vacuum freeze dryer, with vacuum degree controlled to be 30 to 50 Pa, to obtain purified antibacterial peptides.

Determination of Types of Amino Acids:

Types of the amino acids of the antibacterial peptides obtained in Examples 1 and 2 were determined by an automatic amino acid analyzer as follows:

glycine, cysteine, arginine, lysine, histidine, alanine, threonine, aspartic acid, leucine, phenylalanine, serine, glutamic acid, valine, methionine, or tyrosine.

pH: The pH values of the antibacterial peptides in Examples 1 and 2 were 2.63 and 2.77, respectively.

Thermal stability test of the antibacterial peptides:

The antibacterial peptides obtained in Examples 1 and 2 were heated in boiling water bath, respectively, and diameters of inhibition zones was measured, and results are shown in the following table:

| Heating time (min) | 0 | 10 | 20 | 30 | 40 |
|---|---|---|---|---|---|
| Diameter of inhibition zone in Example 1 (mm) | 18.33 | 18.32 | 18.25 | 18.22 | 18.11 |
| Diameter of inhibition zone in Example 2 (mm) | 18.25 | 18.24 | 18.20 | 18.20 | 18.02 |

It can be seen from the above table that a treatment at 100° C. has little effect on antibacterial ability of the antibacterial peptides, and the antibacterial activity remains at 98.79% and 98.74% after 40 min in boiling water bath, which indicates that the antibacterial peptides prepared in the disclosure is not easy to denature after being heated, and has good heat resistance and thermal stability.

II. Extraction of Albumin

The disclosure adopts the pea whey water generated in the pea protein processing process, which mainly contains the albumin, oligosaccharides and other components. In centrifuging, a dish type centrifuger, a horizontal centrifuger or a three-column centrifuger can be used.

Example 1

The disclosure adopts the pea whey water generated in the pea protein processing process, which mainly contains the albumin, oligosaccharides and other components. The steps for extracting are specifically as follows:

1) the centrifuging: centrifuging with the pea whey wastewater as the raw material to separate macromolecular proteins from the pea whey water, which ensures that the albumin and pea oligosaccharides enter a next process without blocking devices while ensuring the molecular weight of the albumin is in a range of 1000 to 5000 Daltons.

2) the controlling temperature and exchanging heat: performing a heat exchange on the centrifuged pea whey wastewater at 45° C., so as to keep the temperature of the whey water stable and make it reach an optimum operating temperature before entering a separation membrane.

3) the performing the microfiltration: performing the microfiltration on the pea whey wastewater after the heat exchange, in which the membrane used in the microfiltration is a silicon carbide membrane with a pore size of 10 nanometers to 30 microns, macromolecular proteins which are not separated by centrifuging in the pea whey water are isolated, and the retentate is removed so that the albumin and the oligosaccharides pass.

4) the performing the nanofiltration: removing 95% of water in the pea whey wastewater after the microfiltration by using a nanofiltration module and adjusting system pressure to be 20 bar and filtration temperature to be 60° C.

5) the performing the ultrafiltration: eluting and separating for 8 times with an ultrafiltration membrane with a molecular weight cut-off of 1000 to 5000 Daltons to separate the albumin from the oligosaccharides and obtain the crude albumin with protein content of 80% to 90% on dry basis and oligosaccharide with dry matter content of 7% to 30%.

6) the performing the secondary nanofiltration: washing the crude albumin, with the water of 95% obtained in the nanofiltration in step 4) added and using a sanitary antipollution nanofiltration membrane, and removing the clean water for washing after the washing is complete and reserving the retentate.

7) the performing the multi-effect concentration: evaporating the retentate using an evaporator with a water evaporation capacity of 1800 kg/h, in which a feed concentration is concentrated from 10% to a discharge concentration of 47%, with a vapor pressure being 0.7 Mpa.

8) the adjusting the pH: adding the alkaline substance and adjusting the pH value to 6.5, with a temperature being 55° C. and dry matter content being of 14%.

9) the sterilizing and drying: sterilizing and deodorizing by a flash device with the temperature controlled to be 140° C., and transporting the protein to a drying system for drying, in which a drying temperature can be adjusted according to products and weather, with an inlet air temperature controlled to be 143° C. and an outlet air temperature controlled to be 55° C.

Example 2

The disclosure adopts the pea whey water generated in the pea protein processing process, which mainly contains the albumin, oligosaccharides and other components. The steps for extracting are specifically as follows:

1) the centrifuging: centrifuging with the pea whey wastewater as the raw material to separate macromolecular proteins from the pea whey water, which ensures that the albumin and pea oligosaccharides enter a next process without blocking devices while ensuring the molecular weight of the albumin is in a range of 1000 to 5000 Daltons.

2) the controlling temperature and exchanging heat includes performing a heat exchange on the centrifuged pea whey wastewater at 40° C., so as to keep the temperature of the whey water stable and make it reach an optimum operating temperature before entering a separation membrane.

3) the performing the microfiltration: performing the microfiltration on the pea whey wastewater after the heat exchange, in which the membrane used in the microfiltration is a silicon carbide membrane with a pore size of 10 nanometers to 30 microns, macromolecular proteins which are not separated by centrifuging in the pea whey water are isolated, and the retentate is reserved so that the albumin and the oligosaccharides pass.

4) the performing the nanofiltration: removing 95% of water in the pea whey wastewater after the microfiltration by using a nanofiltration module and adjusting system pressure to be 20 bar and filtration temperature to be 45° C.

5) the performing the ultrafiltration: eluting and separating for 7 times with an ultrafiltration membrane with a molecular weight cut-off of 1000 to 5000 Daltons to separate the albumin from the oligosaccharides and obtain the albumin with protein content of 80% to 90% on dry basis and oligosaccharide with dry matter content of 7% to 30%.

6) the performing the secondary nanofiltration: washing the crude albumin, with the water of 95% obtained in the nanofiltration in step 4) added and using a sanitary antipollution nanofiltration membrane, and removing the clean water for washing after the washing is complete and reserving the retentate.

7) the performing the multi-effect concentration: evaporating the retentate using an evaporator with a water evaporation capacity of 1800 kg/h, in which a feed concentration is concentrated from 8% to a discharge concentration of 48%, with a vapor pressure being 0.6 Mpa.

8) the adjusting the pH: adding the alkaline substance and adjusting the pH value to 7, with a temperature being 45° C. and dry matter content being of 15%.

9) the sterilizing and drying: sterilizing and deodorizing by a flash device with the temperature controlled to be 140° C., and transporting the protein to a drying system for drying, in which a drying temperature can be adjusted according to products and weather, with an inlet air temperature controlled to be 130° C. and an outlet air temperature controlled to be 48° C.

Example 3

The disclosure adopts the pea whey water generated in the pea protein processing process, which mainly contains the albumin, oligosaccharides and other components. The steps for extracting are specifically as follows:

1) the centrifuging: centrifuging with the pea whey wastewater as the raw material to separate macromolecular proteins from the pea whey water, which ensures that the albumin and pea oligosaccharides enter a next process without blocking devices while ensuring the molecular weight of the albumin is in a range of 1000 to 5000 Daltons.

2) the controlling temperature and exchanging heat: performing a heat exchange on the centrifuged pea whey wastewater at 44° C., so as to keep the temperature of the whey water stable and make it reach an optimum operating temperature before entering a separation membrane.

3) the performing the microfiltration: performing the microfiltration on the pea whey wastewater after the heat exchange, in which the membrane used in the microfiltration is a ceramic membrane, macromolecular proteins which are not separated by centrifuging in the pea whey water are isolated, and the retentate is reserved so that the albumin and the oligosaccharides pass.

4) the performing the nanofiltration: removing 94% of water in the pea whey wastewater after the microfiltration by using a nanofiltration module and adjusting system pressure to be 18 bar and filtration temperature to be 55° C.

5) the performing the ultrafiltration: eluting and separating for 8 times with an ultrafiltration membrane with a molecular weight cut-off of 1000 to 5000 Daltons to separate the albumin from the oligosaccharides and obtain the albumin with protein content of 80% to 90% on dry basis and oligosaccharide with dry matter content of 7% to 30%.

6) the performing the secondary nanofiltration: washing the crude albumin, with the water of 94% obtained in the nanofiltration in step 4) added and using a sanitary antipollution nanofiltration membrane, and removing the clean water for washing after the washing is complete and reserving the retentate.

7) the performing the multi-effect concentration: evaporating washed albumin slurry using an evaporator with a water evaporation capacity of 1800 kg/h, in which a feed concentration is concentrated from 9% to a discharge concentration of 49%, with a vapor pressure being 0.6 Mpa.

8) the adjusting the pH: adding the alkaline substance into a stainless steel tank and adjusting the pH value to 7.8, with a temperature being 42° C. and dry matter content being of 16%.

9) the sterilizing and drying: sterilizing and deodorizing by a flash device with the temperature controlled to be 138° C., and transporting the protein to a drying system for drying, in which a drying temperature can be adjusted according to products and weather, with an inlet air temperature controlled to be 145° C. and an outlet air temperature controlled to be 50° C.

Example 4

The disclosure adopts the pea whey water generated in the pea protein processing process, which mainly contains the albumin, oligosaccharides and other components. The steps for extracting are specifically as follows:

1) the centrifuging: centrifuging with the pea whey wastewater as the raw material to separate macromolecular proteins from the pea whey water, which ensures that the albumin and pea oligosaccharides enter a next process without blocking devices while ensuring the molecular weight of the albumin is in a range of 1000 to 5000 Daltons.

2) the controlling temperature and exchanging heat: performing a heat exchange on the centrifuged pea whey wastewater at 41° C., so as to keep the temperature of the whey water stable and make it reach an optimum operating temperature before entering a separation membrane.

3) the performing the microfiltration: performing the microfiltration on the pea whey wastewater after the heat exchange, in which the membrane used in the microfiltration is a silicon carbide membrane with a pore size of 10 nanometers to 30 microns, macromolecular proteins which are not separated by centrifuging in the pea whey water are isolated, and the retentate is reserved so that the albumin and the oligosaccharides pass.

4) the performing the nanofiltration: removing 95% of water in the pea whey wastewater after the microfiltration by using a nanofiltration module and adjusting system pressure to be 25 bar and filtration temperature to be 58° C.

5) the performing the ultrafiltration: eluting and separating for 10 times with an ultrafiltration membrane with a molecular weight cut-off of 1000 to 5000 Daltons to separate the albumin from the oligosaccharides and obtain the albumin with protein content of 80% to 90% on dry basis and oligosaccharide with dry matter content of 7% to 30%.

6) the performing the secondary nanofiltration: washing the crude albumin, with the water of 95% obtained in the nanofiltration in step 4) added and using a sanitary anti-pollution nanofiltration membrane, and removing the clean water for washing after the washing is complete and reserving the retentate.

7) the performing the multi-effect concentration: evaporating washed albumin slurry using an evaporator with a water evaporation capacity of 1800 kg/h, in which a feed concentration is concentrated from 12% to a discharge concentration of 50%, with a vapor pressure being 0.8 Mpa.

8) the adjusting the pH: adding the alkaline substance into a stainless steel tank and adjusting the pH value to 8, with a temperature being 65° C. and dry matter content being of 18%. 9) the sterilizing and drying: sterilizing and deodorizing by a flash device with the temperature controlled to be 137° C., and transporting the protein to a drying system for drying, in which a drying temperature can be adjusted according to products and weather, with an inlet air temperature controlled to be 135° C. and an outlet air temperature controlled to be 60° C.

Experimental Data:

I. Recycling Rate and Purity of Albumin

The recycling rate and purity of the albumin extracted from Examples 1 to 4 were measured in terms of the recycling rate and the purity respectively, and the purity measurement was made by a conventional Kjeldahl method. Test results are shown in the following table.

| Items | Example | Results |
|---|---|---|
| Recycling rate/% | Example1 | 89% |
| | Example2 | 85% |
| | Example3 | 89% |
| | Example4 | 90% |
| Purity/% | Example1 | 93% |
| | Example2 | 88% |
| | Example3 | 91% |
| | Example4 | 92% |

It can be seen from the above table that the albumin extracted by the method of the present disclosure has high purity, which is between 88% and 93%, and the recycling rate of the albumin in the pea whey water is between 85% and 90%, which indicates that the extraction method of the present disclosure can effectively recycle the albumin with small molecular weight in the pea whey water.

II. Measurement of Molecular Weight Distribution Range

The albumin obtained in Example 1 of the present disclosure and the conventional pea protein peptide were tested for their molecular weight distribution range According to GB/T22492-2008, and results are shown in the following table.

| Molecular Weight Range | Albumin Prepared by Present Disclosure | | | Conventional Pea Protein Peptide | | |
|---|---|---|---|---|---|---|
| | Peak Area Percentage % ($\lambda$ = 220 nm) | Number Average Molecular Weight | Weight Average Molecular Weight | Peak Area Percentage % ($\lambda$ = 220 nm) | Number Average Molecular Weight | Weight Average Molecular Weight |
| >10000 | 3.06 | 15437 | 16357 | / | / | / |
| 10000-5000 | 5.1 | 6497 | 6814 | / | / | / |
| 5000-3000 | 39.65 | 3968 | 4042 | 0.44 | 3657 | 3765 |
| 3000-2000 | 28.19 | 2480 | 2517 | 1.08 | 2340 | 2372 |
| 2000-1000 | 17.16 | 1502 | 1557 | 8.76 | 1270 | 1313 |
| 1000-500 | 1.89 | 710 | 739 | 25.56 | 641 | 667 |
| 500-180 | 2.74 | 286 | 313 | 51.85 | 281 | 303 |
| <180 | 2.21 | / | / | 12.32 | / | / |

It can be seen from the above table that in the albumin prepared by the present disclosure, the albumin with a molecular weight ranging from 1000 to 5000 accounts for 85%, and those with a molecular weight ranging from 180 to 1000 or being larger than 10000 Daltons account for 15%. However, the conventional pea protein peptide has a large molecular weight and a dispersed molecular weight distribution, and the protein peptide with a molecular weight ranging from 1000 to 5000 only accounts for 10.28%, and those with a molecular weight ranging from 180 to 1000 Dalton account for 89.72%. The larger the molecular weight, the harder it is to be absorbed by human body, while the albumin prepared by the disclosure has relatively average and small molecular weight, and is easy to be absorbed and utilized by the human body.

III. Amino Acid Measurement

The amino acid content of the albumin obtained in Example 1 of the present disclosure was determined by high performance liquid chromatography, and results are shown in the following table.

| Amino Acid | Albumin | Pure Albumin | WHO/FAO Standard Model |
|---|---|---|---|
| Cystine Methionine | 4.97 | 5.70 | 3.5 |
| Threonine | 5.48 | 6.00 | 4 |
| Valine | 3.98 | 4.15 | 5 |
| Isoleucine | 2.56 | 2.93 | 4 |
| Leucine | 3.00 | 3.44 | 7 |
| Tyrosine Phenylalanine | 6.63 | 7.61 | 6 |
| Lysine | 8.85 | 10.16 | 5.5 |
| Tryptophan | 0.89 | 1.03 | 1 |

It can be seen from the above table that the albumin obtained by the extraction method of the present disclosure has a complete variety of amino acids and has similar amino acid content with pure albumin. Compared with the WHO/

FAO standard model, except that content of a few amino acids is lower than that of a standard model due to structural limitations of the albumin itself, content of other amino acids exceeds that of the standard model, which indicates that the albumin obtained by the extraction method of the present disclosure has good performance, high nutritional value and good product quality.

The technical scheme of the present disclosure is based on a whole inventive concept, which is an inseparable and cannot be split technically. In the following, an integrity of the disclosure in detail will be explained and verified by experiments.

The pea whey water is centrifuged followed by temperature controlling and heat exchanging so that macromolecular proteins in the pea whey water can be separated, which ensures that the albumin and pea oligosaccharides enter a next process without blocking devices while ensuring so as to ensure that the molecular weight of the separated albumin are concentrated in a range of 1000 to 5000 Daltons and the molecular weight is relatively average. The temperature controlling and heat exchanging were carried out before the microfiltration to keep the temperature of the whey water stable and make it reach an optimum operating temperature before the microfiltration, thus laying a foundation for subsequent effective separation. In the microfiltration, macromolecular proteins that were not separated by centrifuging in the pea whey water were further separated, laying a foundation for the subsequent nanofiltration. If there is no microfiltration, the subsequent nanofiltration membrane will be blocked soon, which will shorten service life and reduce flux, leading to a reduced resulting albumin purity and yield. In the nanofiltration, the nanofiltration module is used to further separate the albumin and remove 93% to 95% of water at the same time, this water can be recycled and used in secondary nanofiltration which removes a sewage treatment process and saves water resources, and after the nanofiltration, the albumin still contains a small amount of oligosaccharides; at this time, the ultrafiltration is carried out to separate the albumin from the oligosaccharides. However, at this time, the albumin still contains excess salt, which leads to a lower albumin purity. Then, the secondary nanofiltration is carried out, in which the sanitary anti-pollution nanofiltration membrane is adopted, and the clean water separated during the nanofiltration is added for washing to elute the excess salt, and after washing is complete, the clean water is separated and recycled. In this scheme, the macromolecular proteins in bean whey water are removed with various separation and water washing processes, which effectively reduces interference of the macromolecular proteins on subsequent albumin separation process and ensures the purity of the albumin. In this process, a desalination process is adopted, in which the salt in the albumin is washed with the water and separated by the nanofiltration membrane to remove sour taste of the whey proteins, so that the albumin is guaranteed with a good mouthfeel. In the separation technology for controlling the molecular weight of the albumin, an ultrafiltration separation system is also adopted, which makes the molecular weight of albumin products relatively average, uniform and controllable.

Comparative Example A: an extraction method is the same as that of Example 1, except that there is no microfiltration.

Comparative Example B: an extraction method is the same as that of Example 1, except that there is no nanofiltration.

Comparative Example B: an extraction method is the same as that of Example 1, except that there is no ultrafiltration.

Comparative Example B: an extraction method is the same as that of Example 1, except that there is no secondary nanofiltration.

The recycling rate and purity of the albumin obtained by the above comparative examples are measured, results are shown in the following table.

| Items | Example | Results |
| --- | --- | --- |
| Recycling rate/% | Example 1 | 89% |
|  | Comparative Example A | 47% |
|  | Comparative Example B | 45% |
|  | Comparative Example C | 0% |
|  | Comparative Example D | 77% |
| Purity/% | Example1 | 93% |
|  | Comparative Example A | 64% |
|  | Comparative Example B | 59% |
|  | Comparative Example C | 0% |
|  | Comparative Example D | 71% |

It can be seen from the above results that when there is no microfiltration and nanofiltration, the recycling rate of the albumin is substantially reduced and the lowest is only 45%, and the purity is also substantially reduced and the lowest is only 59%, while when there is no ultrafiltration, the recycling rate of the albumin is 0, which indicates that it is impossible to separate the albumin with small molecular weight that meets the standard without the ultrafiltration; and when there is no secondary nanofiltration, the purity of the albumin is substantially reduced.

Measurement of the albumin recycling rate at different heat exchange temperatures: Other steps in the experiment are the same as those in Example 1, except that different heat exchange temperatures are adopted, which are 30, 35, 40, 45, 50, 55, 60, 65 and 70° C., respectively, and the related properties of the resulting obtained albumin products are measured, and the results are shown in the following table.

| Items | Temperature | Results |
| --- | --- | --- |
| Recycling rate/% | 30° C. | 0% |
|  | 35° C. | 0% |
|  | 40° C. | 84% |
|  | 45° C. | 89% |
|  | 50° C. | 82% |
|  | 55° C. | 9% |
|  | 60° C. | 8% |
|  | 65° C. | 6% |
|  | 70° C. | 6% |

It can be seen from the above table that the extraction recycling rate of the albumin is 0 at 30 to 40° C., that is, when the heat exchange temperature is lower than 40° C., the albumin cannot be extracted and recycled. In a heat exchange range of the present disclosure, that is, at a temperature of 40 to 50° C., the recycling rate is 82 to 89% and is highest at 45° C. When the temperature is higher than 50° C., the recycling rate of the albumin decreases substantially and all are below 10%, which indicates that with reasonable temperature controlling and heat exchanging, the temperature of the pea whey water can be effectively maintained to be stable and to reach the optimal operating temperature before microfiltration, laying a foundation for subsequent effective separation, thus improving the recycling rate of the albumin.

It can be seen from the above experimental data that a technical scheme of the present disclosure is as a whole and is indispensable. Only when all the processes are incorporates and interlocks with each other, can the high recycling rate and purity of the resulting extracted albumin be guaranteed, in which it is impossible to carry out a simple technical segmentation. It can be seen from the above data that the disclosure can effectively solve the problem that membrane pores are blocked or membrane flux is reduced when the ultrafiltration or the nanofiltration is used for retention individually in the conventional technology for extracting protein peptides, thus effectively reducing investment cost and production cost and facilitating industrial production.

Obviously, specific implementations of the present disclosure is not limited by the above-mentioned ways, and any case where various immaterial modifications are made with the method concept or technical schemes of the present disclosure or any situation where the concept and technical schemes of the present disclosure are directly applied to other occasions without any improvement is within the protection scope of the present disclosure.

What is claimed is:

1. A method for extracting antibacterial peptides from pea whey wastewater, comprising following steps: centrifuging with the pea whey wastewater generated during pea protein processing as raw material; controlling temperature and exchanging heat to adjust temperature of the raw material; sequentially performing a microfiltrating, nanofiltration, ultrafiltration and secondary nanofiltration to obtain an albumin slurry; performing a multi-effect concentrating on the albumin slurry; adding an alkaline substances to adjust pH; sterilizing and drying to obtain the albumin;

adding water to the albumin to obtain another albumin slurry, pretreating in water bath, cooling and stirring on a constant temperature magnetic stirrer, adding papain and dipping alkali solution to keep pH of enzymatic hydrolysate constant; boiling to inactivate enzyme after full enzymolysis and cooling, adjusting the pH to 7.0; centrifuging and concentrating supernatant by rotary evaporation, and sterilizing with a 0.22 μm syringe filter to obtain primary product of the antibacterial peptides; and passing the primary product of the antibacterial peptides through an extractor, which is cleaned and activated in advance with methanol aqueous solution and then cleaned and balanced by aqueous trifluoroacetic acid solution; sequentially passing the methanol aqueous solution and the aqueous trifluoroacetic acid solution through the extractor and collecting penetrating liquid, vacuum concentrating the penetrating liquid by a rotary evaporator to get concentrated antibacterial peptide solution, taking out the concentrated antibacterial peptide solution and freezing at −15° C., and drying the frozen antibacterial peptides in a vacuum freeze dryer to obtain purified antibacterial peptides;

wherein PH value of the antibacterial peptides is 2.56 to 2.78, as measured by a pH meter; and an antibacterial peptide molecule contains glycine, cysteine, arginine, lysine, histidine, alanine, threonine, aspartic acid, leucine, phenylalanine, serine, glutamic acid, valine, methionine, or tyrosine.

2. A method for extracting albumin from pea whey wastewater, comprising following steps: centrifuging with the pea whey wastewater generated during pea protein processing as raw material; controlling temperature and exchanging heat to adjust temperature of the raw material; sequentially performing a microfiltrating, nanofiltration, ultrafiltration and secondary nanofiltration to obtain an albumin slurry; performing a multi-effect concentration on the albumin slurry; adding an alkaline substances to adjust pH; and sterilizing and drying to obtain the albumin.

3. The method for extracting the albumin from the pea whey wastewater according to claim 2, specifically comprising:
   1) the centrifuging: centrifuging with the pea whey wastewater as the raw material;
   2) the controlling temperature and exchanging heat: performing a heat exchange on the centrifuged pea whey wastewater;
   3) the performing the microfiltration: performing the microfiltration on the pea whey wastewater after the heat exchange;
   4) the performing the nanofiltration: removing 93% to 95% of water in the pea whey wastewater after the microfiltration by using a nanofiltration module and adjusting system pressure and filtration temperature;
   5) the performing the ultrafiltration: eluting and separating for 5 to 10 times with an ultrafiltration membrane to obtain a crude albumin slurry;
   6) the performing the secondary nanofiltration: washing the crude albumin with clean water added and using an anti-pollution nanofiltration membrane, and removing the clean water for washing after the washing is complete;
   7) the performing the multi-effect concentration: adding the washed albumin slurry into an evaporator for evaporation and concentration;
   8) the adjusting the pH: adding the alkaline substance into a stainless steel tank and adjusting the pH value; and
   9) sterilizing and drying.

4. The method for extracting the albumin from the pea whey wastewater according to claim 2, wherein the temperature in controlling temperature and exchanging heat is 40 to 50° C.

5. The method for extracting the albumin from the pea whey wastewater according to claim 2, wherein a membrane used in the microfiltration is a silicon carbide membrane or a ceramic membrane.

6. The method for extracting the albumin from the pea whey wastewater according to claim 5, wherein a pore size of the silicon carbide film is 10 nanometers to 30 micrometers.

7. The method for extracting the albumin from the pea whey wastewater according to claim 2, wherein during the nanofiltration, the system pressure is adjusted to 18 to 25 bar, and the filtration temperature is 40 to 65° C.

8. The method for extracting the albumin from the pea whey wastewater according to claim 2, wherein a pore size of an ultrafiltration membrane is configured to provide a molecular weight cut-off of 1000 to 5000 Daltons.

9. The method for extracting the albumin from the pea whey wastewater according to claim 3, wherein during the secondary nanofiltration, the clean water for washing is the water of 93% to 95% obtained in the nanofiltration in step 4).

10. The method for extracting the albumin from the pea whey wastewater according to claim 2, wherein during the multi-effect concentration, a vapor pressure is 0.6-0.8 MPa, and a concentration of the concentrated albumin slurry is 25% to 50%; and during the adjusting the pH, the alkaline substance is added at a temperature of 40 to 65° C. to adjust the pH to be 6.5 to 8.

11. The method for extracting the albumin from the pea whey wastewater according to claim 3, wherein the temperature in controlling temperature and exchanging heat is 40 to 50° C.

12. The method for extracting the albumin from the pea whey wastewater according to claim 3, wherein a membrane used in the microfiltration is a silicon carbide membrane or a ceramic membrane.

13. The method for extracting the albumin from the pea whey wastewater according to claim 3, wherein during the nanofiltration, the system pressure is adjusted to 18 to 25 bar, and the filtration temperature is 40 to 65° C.

14. The method for extracting the albumin from the pea whey wastewater according to claim 3, wherein a pore size of an ultrafiltration membrane is configured to provide a molecular weight cut-off of 1000 to 5000 Daltons.

15. The method for extracting the albumin from the pea whey wastewater according to claim 3, wherein during the multi-effect concentration, a vapor pressure is 0.6-0.8 MPa, and a concentration of the concentrated albumin slurry is 25% to 50%; and during the adjusting the pH, the alkaline substance is added at a temperature of 40 to 65° C. to adjust the pH to be 6.5 to 8.

\* \* \* \* \*